(12) United States Patent
Chernoff

(10) Patent No.: US 7,232,456 B2
(45) Date of Patent: Jun. 19, 2007

(54) TISSUE TREATMENT METHOD

(76) Inventor: W. Gregory Chernoff, 5846 N. LaSalle, Indianapolis, IN (US) 46220

( * ) Notice: Subject to any disclaimer, the term of this patent is extended or adjusted under 35 U.S.C. 154(b) by 31 days.

(21) Appl. No.: 09/785,715

(22) Filed: Feb. 16, 2001

(65) Prior Publication Data

US 2001/0007079 A1    Jul. 5, 2001

Related U.S. Application Data

(63) Continuation of application No. 09/173,990, filed on Oct. 16, 1998, now abandoned.

(60) Provisional application No. 60/063,754, filed on Oct. 17, 1997.

(51) Int. Cl.
*A61N 5/067* (2006.01)
*A61B 18/22* (2006.01)

(52) U.S. Cl. .............................. 607/89; 607/88; 606/9; 128/898

(58) Field of Classification Search .................. 606/2, 606/7–9; 424/443; 128/898; 607/88–92
See application file for complete search history.

(56) References Cited

U.S. PATENT DOCUMENTS

| 4,838,253 | A |   | 6/1989 | Brassington et al. |
| 4,991,574 | A | * | 2/1991 | Pocknell ...................... 128/156 |
| 5,500,019 | A | * | 3/1996 | Johnson et al. ................. 623/8 |
| 5,552,162 | A | * | 9/1996 | Lee ............................ 424/646 |
| 5,624,435 | A | * | 4/1997 | Furumoto .................... 606/10 |
| 5,720,772 | A |   | 2/1998 | Eckhouse |
| 5,741,509 | A | * | 4/1998 | Kushner ..................... 424/443 |
| 5,759,560 | A |   | 6/1998 | Dillon |
| 5,765,567 | A | * | 6/1998 | Knowlton ................... 128/898 |
| 5,766,233 | A |   | 6/1998 | Thiberg |
| 5,891,076 | A |   | 4/1999 | Fabo |
| 5,895,656 | A |   | 4/1999 | Hirshowitz et al. |
| 5,897,549 | A | * | 4/1999 | Tankovich ...................... 606/9 |
| 5,919,476 | A |   | 7/1999 | Fischer et al. |
| 5,948,822 | A |   | 9/1999 | Pope et al. |
| 6,337,076 | B1 | * | 1/2002 | Studin ........................ 424/401 |
| 6,503,246 | B1 | * | 1/2003 | Har-Shai et al. .............. 606/23 |
| 6,572,878 | B1 | * | 6/2003 | Blaine ........................ 424/443 |

FOREIGN PATENT DOCUMENTS

WO    WO 01/26606 A2 *  4/2001

* cited by examiner

*Primary Examiner*—A. Farah
(74) *Attorney, Agent, or Firm*—Barnes & Thornburg LLP

(57) ABSTRACT

A method of treatment of a scar comprising applying a topical silicone gel to the scar, and wiping off the excess to leave a thin layer of the gel on the scar. Applications of the topical silicone gel can be alternated with applications of silicone gel sheeting to the scar. The method may further include treating the scar with laser therapy.

7 Claims, No Drawings

TISSUE TREATMENT METHOD

This disclosure is a continuation of U.S. patent application Ser. No. 09/173,990, which was filed on Oct. 16, 1998, is now abandoned, and claimed priority to U.S. Provisional Application No. 60/063,754, filed on Oct. 17, 1997.

BACKGROUND OF THE INVENTION

Hypertrophic scars and keloids affect an estimated 10% of the population. While a variety of therapeutic modalities have been attempted, the majority of medical and surgical specialties treating these problems agree that these are notoriously difficult to treat. Currently over 50% of our population is aged forty-five years or older. With more minimally invasive procedures becoming available, more patients seek elective aesthetic surgical procedures. With cutaneous laser exfoliation procedures on the rise, there has also been an increased incidence of facial hypertrophic scars. While more deeply pigmented skin is susceptible, any person may develop a persistent hypertrophic scar or keloid following a traumatic injury or surgical intervention. These types of scars are more common in areas which demonstrate slow wound healing response, such as the anterior chest, and in movement-dependent areas, such as the scapula, elbow, and knee. A hypertrophic scar is usually raised and erythematous, but remains within the confines of the original traumatic wound. In contrast, a keloid is a more nodular lesion which extends beyond the margins of the initial wound.

For centuries physicians have studied the processes of wound healing. Wound healing is complicated, but generally can be divided into three overlapping phases. There is an inflammation phase, a granulation tissue formation phase, and a matrix formation or remodeling phase. Studies have revealed that these phases overlap. Considerable study has gone into the modification of these phases, with the hope of gaining some control over the overall wound healing mechanism. For decades, scars were an accepted phenomenon. Patients were told that there was little that could be done, and had to come to accept the appearance of their scars. Many patients have stimulated the interest of researchers to attempt to modify the healing process, since many patients do not readily accept that nothing can be done to improve the appearance of what they may perceive as somewhat disfiguring scars.

A general understanding of the phases of healing is important to an understanding of scar modification parameters. The first phase of wound healing is the inflammatory phase. During this stage, there is a release of mediators which sets the stage for the formation of granulation tissue. This inflammatory phase can be divided into an early and a late period. The early period starts immediately with the wounding of the skin. The initial trauma causes bleeding into the wound space. Subsequent to normal hematosis, the exposure of blood to fibrillar collagen and tissue factor starts the intrinsic and extrinsic clotting cascades. The aggravation of platelets also triggers the coagulation cascade and contributes to hemostasis. The habradic kinen is released through activated factor 12. This stimulates the classic compliment cascade to begin. This subsequently causes the release of anaphylatoxins and subsequent vascular permeability-ability with chemotaxis of white blood cells.

During the early portion of the inflammatory phase neutrophils and monocytes appear in the wound space. First, neutrophils appear approximately six hours after the insult. Monocytes arrive somewhat later. The main function of the neutrophils in early wound healing is to debride the wound of particulate and bacterial contamination. The disappearance of neutrophils from the wound space signals the end of the early inflammatory phase of wound healing. This is usually seen within one to two days.

In contrast to the neutrophil, monocytes persist in the wound space and play a more significant role. The persistence of macrophages marks the late segment of the inflammatory phase. Macrophages continue with the debridement of the wound by phagocytizing bacteria and debris.

The second phase of wound healing, known as the granulation phase, is characterized by granulation tissue formation. Within the granulation phase of wound healing, the processes of angiogenesis, re-epithelialization and collagen synthesis occur. The main cells involved in this phase include macrophages, the fibroblasts, epithelial cells and endothelial cells. These cells work together under the direction of growth factors and other mediators. Extracellular matrix is also formed during this phase. This matrix which is comprised of fibronectin and collagen is a critical component to the wound healing. Extracellular matrix is composed primarily of proteoglycans, fibronectin, and collagen. The aforementioned cells act in unison to facilitate the processes of re-epithelialization and neovascularization.

Remodeling is the third and final phase of wound healing. It is during this phase that the extracellular matrix is reorganized and collagen converted from type 3 collagen to type 1 collagen. It is during this phase that wound contraction also occurs. Wound contraction involves a complex interaction between fibroblasts, fibronectin, and collagen. Several models of remodeling suggest that fibroblasts are recruited into the wound via the chemotactic properties of various growth factors. Once a critical mass of fibroblasts exists within the wound, fibronectin and type 1 collagen are then produced. Fibroblasts align themselves within the fibronectin-collagen extracellular lattice. Wound contraction can then occur through this tightly arranged network of fibroblast, fibronectin, and collagen.

As the remodeling phase continues, fibronectin disappears from the wound and is replaced by collagen. Collagen continues to occupy more of the wound space and the wound breaking strength begins to increase. As type 1 collagen surpasses type 3 collagen, the breaking strength once again shows an increase. Typically a final scar ultimately obtains a breaking strength 70% that of uninjured skin.

A variety of treatments for hypertrophic scars and keloids have been advocated in the past. These include intralesional steroids, cryosurgery, radiotherapy, pressure therapy, silicone gel sheeting, laser therapy, and excisional surgery. Recurrences remain common, and patient satisfaction is variable. Many patients are also dissatisfied with the increased erythema in the wound.

DETAILED DESCRIPTION OF AN ILLUSTRATIVE EMBODIMENT

A silicone gel, a polysyloxane derivative, is examined for efficacy in the management of hypertrophic scars and wound erythema. This study examines a four year prospective analysis involving one hundred patients with one hundred and forty scars. Thirty patients with more than one scar permitted the utilization of one of the scars as a control group to which no treatment was provided. This group was compared to a group utilizing silicone gel alone, silicone gel sheeting alone, and the combination of silicone gel, silicone gel sheeting, intralesional steroid injections, and vascular laser therapy.

Subsequent analysis included profilomety analysis of scar regions, punch biopsies of the control and therapy scars as well as subjective analysis by physician and patient.

Results revealed comparable resolution and improvement of healing scars, hypertrophic scars, and excised keloids when utilizing silicone gel alone. Improvement in erythema was also realized. Collagen reorientation was demonstrated histologically.

A significant advantage of silicone gel is its ease of application and effortless maintenance. When a small amount of the polymer is applied, the molecules orient themselves one layer thick once the excess is wiped away from the affected area. Topical silicone gel provides an acceptable addition in the armamentarium of the treatment of healing wounds for areas where application of gel sheeting products is difficult and often awkward for the patient.

The potential efficacy of topical silicone gel in the treatment of hypertrophic scars, keloid scars, and erythema was investigated. An advantage of topical silicone gel is its ease of application and effortless maintenance. It has been shown that application of a small amount of the polymer causes a molecular orientation which can provide a similar pressure effect to silicone gel sheeting.

One hundred consecutive patients who presented for scar revision were treated. Sixty-four were females and thirty-six were males. This patient population exhibited one hundred forty scars for the purposes of examination. The scars that were deemed appropriate for this study were scars which were still in the erythematous and raised phase, hypertrophic scars, and keloid scars. Scars which were deemed mature by virtue of their flatness, lack of erythema, or lack of pigmentation, were not treated as part of this study.

Of the one hundred and forty scars, seventy-one were located on the face, eight on the neck, five on the sternum, ten on the breast, twenty-five on the abdomen, nine on the arms, eleven on the legs, and one on the buttock.

Thirty of the patients in the population had scars in more than one location which permitted one scar to serve as a control for comparison to the therapeutic regime. These thirty patients were divided into three groups. A first group had a topical polysiloxane gel applied periodically to a treatment scar, and no treatment to a control scar. A polysiloxane derivative that is marketed under the trade name Kelo-cote was chosen as the topical silicone gel. Kelo-Cote brand polysiloxane derivative is as described in U.S. Pat. No. 5,741,509. Treated and control scars were then examined for erythema, elevation, and overall softening at thirty days, sixty days, and ninety days. A second group had silicone gel sheeting applied. The second group was also evaluated at 30, 60, and 90 days. A third group had intralesional corticosteroids, followed by vascular laser therapy on a six weekly basis. This group was also examined at 30, 60 and 90 days.

The remaining sixty scars were divided into two groups. One group had a combination of topical silicone gel application during the day followed by silicone gel sheeting at night. The second croup employed topical silicone gel during the day, silicone gel sheeting at night, intralesional steroid injections and vascular laser therapy every six weeks. These two groups were also evaluated at 30, 60, and 90 days. Histological biopsies were obtained, examining specifically the orientation of the collagen fibers in relation to subjective measures of healing of the scar.

The group of patients with more than one scar provided a unique control for comparison with treatment regimes. Skin surface texture was measured objectively utilizing computer-assisted digital imaging (optical profilometry). The group of patients who received topical silicone gel treatment compared favorably with the group treated using silicone gel sheeting, showing comparable leveling of the hypertrophic or healing scar, as well as decreased erythema. These findings were most evident at ninety days. This result was statistically significant to a P value of 0.01. Perceived softening of the scars by the patients was also comparable. However the silicone gel sheeting group was visibly reduced by sixty days, compared to the ninety days for the topical silicone gel treatment. It was noted that the patients who had experience with both topical silicone gel treatment and silicone gel sheeting rated the topical silicone gel treatment far superior for its ease of application. Importantly, this may be reflected in the patients' willingness to comply with a treatment regime. Facial scars appeared to respond most favorably to topical silicone gel treatment in comparison to treatment with silicone gel sheeting. Scars which were on movement-dependent regions, such as lateral chest, near the shoulder or over joints, responded significantly better to the gel sheeting.

Scars treated with either the topical silicone gel or the silicone gel sheeting exhibited no symptoms associated with scar treatment, whereas 60% of the control scars were symptomatic. There was overall reduced scar erythema among scars treated with either the topical silicone gel or the silicone gel sheeting, compared to no change in erythema for the control scars. There was a mean decreased scar height of 1.5 mm. as compared to a mean scar height of 3.4 mm. among the controls. There was an increase in pliability among scars treated with either the topical silicone gel or the silicone gel sheeting, compared to no change in pliability among the controls. Overall skin texture was improved, as compared to a baseline of no change in skin texture among the controls. Histologically the collagen appeared looser and was more parallel to the surface of the skin, compared to the thick, hylenized collagen of the controls. Histologically, an increased number of mast cells were also observed in the topical silicone gel and silicone gel sheeting populations. Mast cells are important in the remodeling phase. No increase in the number of mast cells was observed in the control group.

The third group of patients were asked to wear the silicone gel sheeting at night and apply the topical silicone gel during the day. When compared to either treatment modality alone, this treatment provided a faster rate of erythema resolution as well as more rapidly decreasing scar height. These results were statistically significant to a P value of 0.01. Half of these also received flash lamp pumped pulse dye laser therapy at 585 nm. with energy densities ranging 6.0-7.5 joules per centimeter squared and spot sizes of 5 or 7 mm. The other half of these received long pulsed green light laser therapy at 532 nm., 50 millisecond pulse widths and a 5 mm. spot size. The third group also received 0.2 cc. of Kenalog-10 immediately after laser therapy. The third group, when compared to the first two groups, revealed further improvements in erythema, scar height, pliability, skin texture and increased numbers of mast cells.

These findings suggest that optimal therapy for scars in various regions of the body entails close to 24 hour application of combinations of the silicone gel sheeting and silicone gel with regular vascular laser therapy to the scars.

Of the remaining patients with single scars in the aforementioned locations, multiple therapy utilizing all of the modalities in questions was employed. Some patients found it easier to apply the silicone gel at night, particularly in regions where movement would cause the gel sheeting to fall off. This patient population showed over an 80% improvement in all the factors previously described as pertains to the qualitative changes of their scars.

It has long been known that pressure therapy to healing scars or hypertrophic scars can yield acceleration of the remodeling phase of healing. A drawback to topical silicone gel sheeting was the difficulty that many patients had in keeping this adherent through the night without a great amount of taping. Patients also refused for the most part to wear gel sheeting during the day when the wound was on a facial area, as the silicone gel sheeting is very noticeable when applied. Topical silicone gel adds an important element to the armamentarium of the physician treating healing wounds or hypertrophic scars. A great advantage of topical silicone gel is its ease of application and effortless maintenance. When a small amount is applied, the molecules orient themselves in a thin layer once the excess is wiped away from the affected area. This, it is believed, has somewhat the same effect as the silicone gel sheeting. A considerable advantage of this compound is its ease of use. It is believed that this increases the compliance of the patient who is utilizing it. The end result of this therapy is improvement in scar height and decreased erythema, with improved skin texture and increased pliability. Histological examination of the scar tissue consistently showed the expected decrease in sclerotic collagen.

The mechanism by which healing scars and hypertrophic scars are altered by this method is unknown. It may be that pressure on the region being remodeled helps to align the extracellular latticework and subsequently allows the fibroblasts to align the collagen more parallel to the surface of the skin. Similar long-term results are attained with vascular laser therapy. Through selective photothermolysis, selective absorption of light by hemoglobin leads to local heating of cutaneous blood vessels, which is confined by the utilization of sufficiently short laser pulse durations. Irreversible, selective thermal injury of vessels leads to subsequent thrombosis, vasculitis, and gradual local repair including neovascularization. Vascular laser destruction likely leads to temporary eschemia which can affect collagen composition, metabolism and the release of collagenase. It is also possible that increasing the numbers of mast cells can lead to improvement in the remodeling phase.

Interestingly, patients' own assessments of their scars were heavily weighted towards improvement when utilizing the combination of the silicone gel sheeting and topical silicone gel. As we are attempting to improve the patient's self-esteem, this is perhaps the most significant result of this trial.

The invention claimed is:

1. A method of treatment of a scar comprising treating the scar with laser therapy with energy densities ranging from about 6.0 joules per centimeter squared to about 7.5 joules per centimeter squared, and applying a topical fluid silicone gel not released from silicone gel sheeting to the scar.

2. A method of treatment of a scar comprising treating the scar with laser therapy with spot sizes in the range of about 5 mm. to about 7 mm, and applying a topical fluid silicone gel not released from silicone gel sheeting to the scar.

3. A method of treatment of a scar comprising treating the scar with laser therapy with energy having wavelengths in the range of about 585 nm, and applying a topical fluid silicone gel not released from silicone gel sheeting to the scar.

4. A method of treatment of a scar comprising treating the scar with laser therapy with energy having wavelengths in the range of about 532 nm, and applying a topical fluid silicone gel not released from silicone gel sheeting to the scar.

5. A method of treatment of a scar comprising treating the scar with long pulsed laser therapy, and applying a topical fluid silicone gel not released from silicone gel sheeting to the scar.

6. The method of claim 5 wherein the step of treating the scar with laser therapy comprises treating the scar with pulsed laser therapy having pulse widths in the range of about 50 milliseconds.

7. The method of claim 6 wherein the step of treating the scar with laser therapy comprises treating the scar with laser therapy with spot sizes in the range of about 5 mm.

\* \* \* \* \*